United States Patent [19]

Shigyo et al.

[11] Patent Number: 5,564,012

[45] Date of Patent: Oct. 8, 1996

[54] SUPPORT APPARATUS FOR USE WITH RADIATION IMAGE INFORMATION PROCESSING SYSTEM

[75] Inventors: Masao Shigyo; Kunimasa Shimizu, both of Kanagawa-ken, Japan

[73] Assignee: Fuji Photo Film Co., Ltd., Kanagawa, Japan

[21] Appl. No.: 470,049

[22] Filed: Jun. 6, 1995

Related U.S. Application Data

[62] Division of Ser. No. 92,981, Jun. 28, 1993, which is a continuation of Ser. No. 500,349, Mar. 28, 1993, abandoned.

[30] Foreign Application Priority Data

| Mar. 29, 1989 | [JP] | Japan | 1-77293 |
| Apr. 20, 1989 | [JP] | Japan | 1-101066 |
| Apr. 20, 1989 | [JP] | Japan | 1-101067 |
| Aug. 1, 1989 | [JP] | Japan | 1-200807 |
| Sep. 25, 1989 | [JP] | Japan | 1-248632 |

[51] Int. Cl.$^6$ .............................. G01R 31/28; G06F 11/00
[52] U.S. Cl. .............................. 395/182.13; 395/183.22; 364/413.13
[58] Field of Search .................. 395/182.13, 183.22; 364/413.13, 413.15

[56] References Cited

U.S. PATENT DOCUMENTS

| 3,729,715 | 4/1973 | Buedel | 340/172.5 |
| 3,953,717 | 4/1976 | Rottier | 395/183.22 |
| 4,305,125 | 12/1981 | Sato et al. | 364/200 |
| 4,377,000 | 3/1983 | Staab | 371/11 |
| 4,437,161 | 3/1984 | Anderson | 364/413.23 |
| 4,458,267 | 7/1984 | Dolazza | 358/111 |
| 4,514,846 | 4/1985 | Federico et al. | 371/16 |
| 4,611,247 | 9/1986 | Ishida et al. | 364/413.13 |
| 4,628,443 | 12/1986 | Rickard et al. | 364/186 |
| 4,628,531 | 12/1986 | Okamoto et al. | 382/8 |
| 4,631,658 | 12/1986 | Easthill | 364/184 |
| 4,740,969 | 4/1988 | Fremont | 371/12 |
| 4,814,969 | 3/1989 | Kiyooka | 364/186 |
| 4,853,946 | 8/1989 | Elliott et al. | 378/4 |
| 4,887,162 | 12/1989 | Arai | 358/400 |
| 4,903,310 | 2/1990 | Takeo et al. | 364/413.13 |
| 4,912,711 | 3/1990 | Shiramizu | 371/16.1 |
| 4,969,049 | 11/1990 | Mitani et al. | 358/296 |
| 5,077,768 | 12/1991 | Shigyo et al. | 378/98 |
| 5,090,040 | 2/1992 | Lanza et al. | 364/413.15 |

FOREIGN PATENT DOCUMENTS

| 55-12429 | 1/1980 | Japan. |
| 55-87970 | 7/1980 | Japan. |
| 55-103472 | 8/1980 | Japan. |
| 55-116340 | 9/1980 | Japan. |

OTHER PUBLICATIONS

*Dictionary of Computers, Information Processing, and Telecommunications,* Rosenberg, copyright 1994, p. 584.

Primary Examiner—Robert W. Beausoliel, Jr.
Assistant Examiner—Glenn Snyder
Attorney, Agent, or Firm—Sughrue, Mion, Zinn, Macpeak & Seas

[57] ABSTRACT

A radiation image information processing system subjects a radiation image to certain signal processing so as to obtain image signal and generates a visible image from the image signal. A support apparatus for the system is composed principally of a control unit, a radiation signal storage unit, a display and a keyboard. When a fault occurs in the radiation image information processing system, a support apparatus is connected to a control apparatus of the system. The fault of the system is detected by the support system, which generates a fault detection signal. An image signal which leads to occurrence of the fault or the like is stored in a memory and thereafter, the analysis of the fault is carried out based on the contents stored. In view of the analyzed contents, the fault is removed and hence the system is recovered.

9 Claims, 3 Drawing Sheets

SUPPORT APPARATUS FOR USE WITH RADIATION IMAGE INFORMATION PROCESSING SYSTEM

This is a divisional of application Ser. No. 08/092,981 filed Jun. 28, 1993, which is a continuation of application Ser. No. 07/500,349 filed Mar. 28, 1990, now abandoned.

BACKGROUND OF THE INVENTION

FIELD OF THE INVENTION

The present invention relates to a support apparatus for use with a radiation image information processing system which reads radiation image signals from a sheet-like storage type phosphor, subjects the same to certain image processing and displays the processed radiation image signals on a photographic film or on a CRT or the like.

In recent years, radiation image information systems have been widespread particularly in the medical field, which are each for recording/reproducing a radiation transmission image of an object such as a human body using a sheet (hereinafter called "storage type phosphor sheet" or merely "sheet") having a layer composed of a storage type phosphor. The radiation image information processing systems have been disclosed in a number of patent applications filed by the present applicant, for example, in Japanese Patent Laid-Open Nos. 55-12429, 55-103472, 55-116340, 55-87970, etc.

When a certain phosphor is exposed to a radiation (such as X-rays, α-rays, β-rays, γ-rays, electron beams, or ultraviolet rays), the phosphor stores a part of the energy of the radiation. When the phosphor exposed to the radiation is subsequently exposed to stimulating rays such as visible light, the phosphor emits accelerated light in proportion to the stored energy of the radiation. The phosphor exhibiting such a property is referred to as "storage type phosphor". In the radiation image information processing system employing the storage type phosphor sheet, the image information about the radiation-transmitted image of an object such as a human body is temporarily stored in a storage type phosphor layered on a sheet (this is subsequently expressed as "the image information is stored in the sheet"), and then the sheet is scanned with stimulating rays such as a laser beam, so that the sheet emits accelerated light. The emitted light is photoelectrically read to produce an information signal (hereinafter called merely "image signal") representative of the radiation-transmitted image. After the image signal have been subjected to certain signal processing, the image signal is displayed as a visible image on a recording medium such as a photographic photosensitive material or on a CRT or the like.

In addition, in the system of this type, it is necessary to carry out a relatively fine adjustment of the state of operation of the system upon installation of the radiation image information processing system. This is because it is required to adjust the system in such a way that the quality in image becomes a desired state in the image visual-recognition analytical work of the conditions of environment at a position where the system is installed or in the image visual-recongnition analytical work using a recording medium or a device with a CRT or the like.

For purposes of adjustment of the system at the time the working for its installation is made, it is practiced to photographically record in practice, for example, an artificial body formed with a human bone or the like upon installation of the radiation image information processing system and then adjust the system based on the recorded image information. It has also been required to perform the working for the installation of the system within a short period of time. Thus, there is a potential problem that inconvenience such as increase in a burden on the economy for provision of servicemen as well as the provision of a large number of servicemen takes place.

When it is desired to record such information on the sheet or to reproduce it on the CRT or the like, it is required to properly keep the state of fine operation of the system. Accordingly, the structure of the support for the system has been kept in order to assist the support of system functions. Under this type of support structure of the system functions, when a fault occurs in the radiation image information processing system, a serviceman or the like inspects the system, and repairs the defective device on site if possible. If it is found to be hard to ascertain the fault on site and the repair for its recovery cannot be performed on site, then a part of a device related to the position where the fault has occurred is replaced with a new one.

However, the storage of chronological data regarding the system failure often tends to be insufficient on the side of the user in the conventional radiation image information processing system. There is also a case where a film on which improper images representing chronological data concerning the system failure or the like have already been recorded is lost. In such a case, it therefore becomes impossible to analyze the cause of the fault, thereby causing a problem.

Furthermore, the visible image obtained in the above-described manner is subjected to a diagnosis by a doctor or the like. However, the condition of image processing is generally different in terms of positions of a part to be diagnosed or a hospital or the like. For example, when one attempts to change parameters for each photographic recording and output the result, the operation of establishing the parameters not only becomes extremely cumbersome but also becomes required to establish the same with a considerable skill. In the case where the condition of the image processing is established once and an image has been recorded on a photographic film, the reestablishment of the image processing condition after the photographic recording is performed again is practically impossible because of an excessive exposure of radiation to a patient.

As an alternative to the above case, it may also be feasible to consider a case where after the radiation image obtained by photographically recording an object is temporarily stored in a recording medium such as a hard disk, a serviceman or the like adjusts the image processing condition and then establishes the image processing condition when the optimal image is obtained. However, this case gives, to the user, inconvenience that the condition of the image processing cannot arbitrarily be adjusted.

When it is desired to monitor the state of operation of the system in the above-described system, for example, when one attempts to test the state of operation of the system at the time a fault has occurred, the state of its operation can heretofore be tested only within the range of processing capability of a known control system in the above-described system. Accordingly, time required to find out a position where the fault has occurred needs a long period of time, thereby causing a drawback.

SUMMARY OF THE INVENTION

It is a principal object of the present invention to provide a support apparatus for use with a radiation image information processing system, which smoothly operates the system where a radiation image signal is read from a storage type phosphor formed on a sheet or the like and then subjected to certain image processing, followed by display of the result on a photographic film or on a CRT or the like.

Another object of the present invention is to provide a support apparatus for use with a radiation image information processing system, wherein where it is desired to perform adjustment of the system by the serviceman, i.e., the initial adjustment at the time of installation of the system or readjustment of the system when it is in operation, with a view toward keeping desired functions of the radiation image information processing system, the support apparatus for the radiation image processing system, in which the reference image has been stored in advance, is connected to the radiation image information processing system, an image obtained from the apparatus is rendered visible so as to be the reference visible image to be used, and then adjustment is made using such a reference visible image in such a way that the quality in image becomes a desirable state in the image visual-recognition analytical work of the conditions of environment at the position where the system is installed or in the image visual-recognition analytical work, using a recording medium or a device with a CRT or the like, performed by the user of the system, thereby making it possible to achieve the desired functions of the system as rapid as practicable.

A further object of the present invention is to provide a support apparatus for use with a radiation image information processing system, wherein where a fault occurs in the radiation image information processing system and thereafter difficulties are encountered on site upon confirmation of a position where the fault has occurred, a dedicated support apparatus for the system is connected to the system and image signals which lead to generation of the fault during a predetermined period of time subsequent to its connection are stored in memory areas, followed by analysis of the fault based on the contents of the stored image signals and the fault or the like is removed, i.e., the recovery and repair of the system is carried out in view of the contents of its analysis, whereby a quick recovery is made and the operation of the system can smoothly be accelerated.

A still further object of the present invention is to provide a support apparatus for use with a radiation image information processing system, which temporarily stores image information obtained from the system therein and thereafter processes the same based on various image processing parameters into an optimal image, and allows, for example, the user himself to establish desired parameters based on the optimal image.

A still further object of the present invention is to overcome the foregoing problems and to provide a support apparatus for use with a radiation image information processing system, wherein where a fault occurs in the radiation image information processing system and thereafter difficulties are encountered on site upon confirmation of a position where the fault has occurred, a dedicated support apparatus for the system is connected to the system and image signals which lead to generation of the fault during a predetermined period of time subsequent to its connection are stored in memory areas, followed by analysis of the fault based on the contents of the stored image signals and the fault or the like is removed, i.e., the recovery and repair of the system is carried out in view of the contents of its analysis, whereby a quick recovery is made and the operation of the system can smoothly be accelerated.

A still further object of the present invention is to provide a support apparatus for use with a radiation processing system, wherein where it is desired to monitor the state of operation of the radiation image information processing system, a support control board with a test program incorporated therein and a bus monitor board are connected to the system, and data on the bus line, which is obtained by executing the test program, is stored in the storing means, and then the state of operation of the system is monitored in detail based on the data, thereby making it possible to find out the fault or promote efficiency in development of a new program.

A still further object of the present invention is to provide a support apparatus for use with a radiation image information processing system, the support apparatus being connected to a radiation image information processing system which subjects a radiation image to certain signal processing so as to obtain an image signal and generates a visible image from the image signal, the support apparatus comprising a control unit for storing therein an image signal at the time a fault occurs and for sending the stored image signal to the radiation image information processing system and means for storing an image signal therein.

A still further object of the present invention is to provide a support apparatus for use with a radiation image information processing system wherein the control unit and the means both comprise transfer recognizing means for recognizing a point in time at which each of image signals is transferred when the control unit constituting the radiation image information processing system is in operation, storing means including a plurality of memory areas for storing the image signals therein, memory establishing means for storing image signals in the storing means based on the result of recognition of the transfer point by the transfer recognizing means, selection storing/holding means for selectively storing/holding the image signals stored in the storing means, and image signal supplying means for supplying the image signals stored in the storing means.

A still further object of the present invention is to provide a support apparatus for use with a radiation image information processing system wherein the storing means makes use of an image memory, and the memory establishing means, the selection storing/holding means and the image signal supplying means each include a keyboard.

A still further object of the present invention is to provide a support apparatus for use with a radiation image information processing system, the support apparatus being connected to a radiation image information processing system which subjects a radiation image to signal processing so as to obtain an image signal and generates a visible image from the image signal, the support apparatus comprising a control unit for ascertaining the state of operation of the system based on data regarding execution of a test program which has been stored therein and means for storing an image signal therein.

A still further object of the present invention is to provide a support apparatus for use with a radiation image information processing system wherein the control unit comprises first storing means for storing a test program therein and operational processing means for executing the test program, and the means includes second storing means for storing data on a bus line provided in the radiation image information processing system therein, based on the test program, and wherein the state of operation of the system is monitored based on the data stored in the second storing means.

A still further object of the present invention is to provide a support apparatus for use with a radiation image information processing system wherein the second means makes use of an image memory.

A still further object of the present invention is to provide a support apparatus for use with a radiation image information processing system which subjects a radiation image to certain signal processing to obtain an image signal and generates a visible image from the image signal, the apparatus comprising a control unit for storing and holding a reference image signal therein and for selectively sending the stored reference image signal therefrom and means for storing an image signal therein.

A still further object of the present invention is to provide a support apparatus for use with a radiation image information processing system wherein the control unit and the means both comprise storing means for storing an image signal having reference quality therein upon initial adjustment of the system at the time the radiation image information processing system is installed or upon readjustment of the system while it is in operation, image signal selecting means for selectively reading out the image signal stored in the storing means upon the initial adjustment or readjustment, image signal supplying means for supplying the image signal stored in the storing means to generate the visible image therefrom with the radiation image information processing system, and parameter establishing means for establishing each of image processing parameters relative to the image signal employed in the radiation image information processing system.

A still further object of the present invention is to provide a support apparatus for use with a radiation image information processing system wherein the storing means makes use of an image memory, and the parameter establishing means includes a keyboard.

A still further object of the present invention is to provide a support apparatus for use with a radiation image information processing system, the support apparatus being connected to a radiation image information processing system which subjects a radiation image to certain signal processing so as to obtain an image signal and generates a visible image from the image signal, the support apparatus comprising a control unit for storing image information therein and for electrically processing the stored image information based on image parameters and means for storing an image signal therein.

A still further object of the present invention is to provide a support apparatus for use with a radiation image information processing system wherein the control unit and the means both comprise storing means for storing a reference image signal supplied from the radiation image information processing system therein, image signal supplying means for supplying the image signal stored in the storing means to generate the visible image therefrom with the radiation image information processing system, and parameter establishing means for establishing image processing parameters relative to the image signal employed in the radiation image information processing system.

A still further object of the present invention is to provide a support apparatus for use with a radiation image information processing system wherein the storing means makes use of an image memory, and the image signal supplying means and the parameter establishing means each include a keyboard.

The above and other objects, features and advantages of the present invention will become apparent from the following description and the appended claims, taken in conjunction with the accompanying drawings in which a preferred embodiment of the present invention is shown by way of illustrative example.

DETAILED DESCRIPTION OF THE PREFERRED EMBODIMENTS

Figure 1:
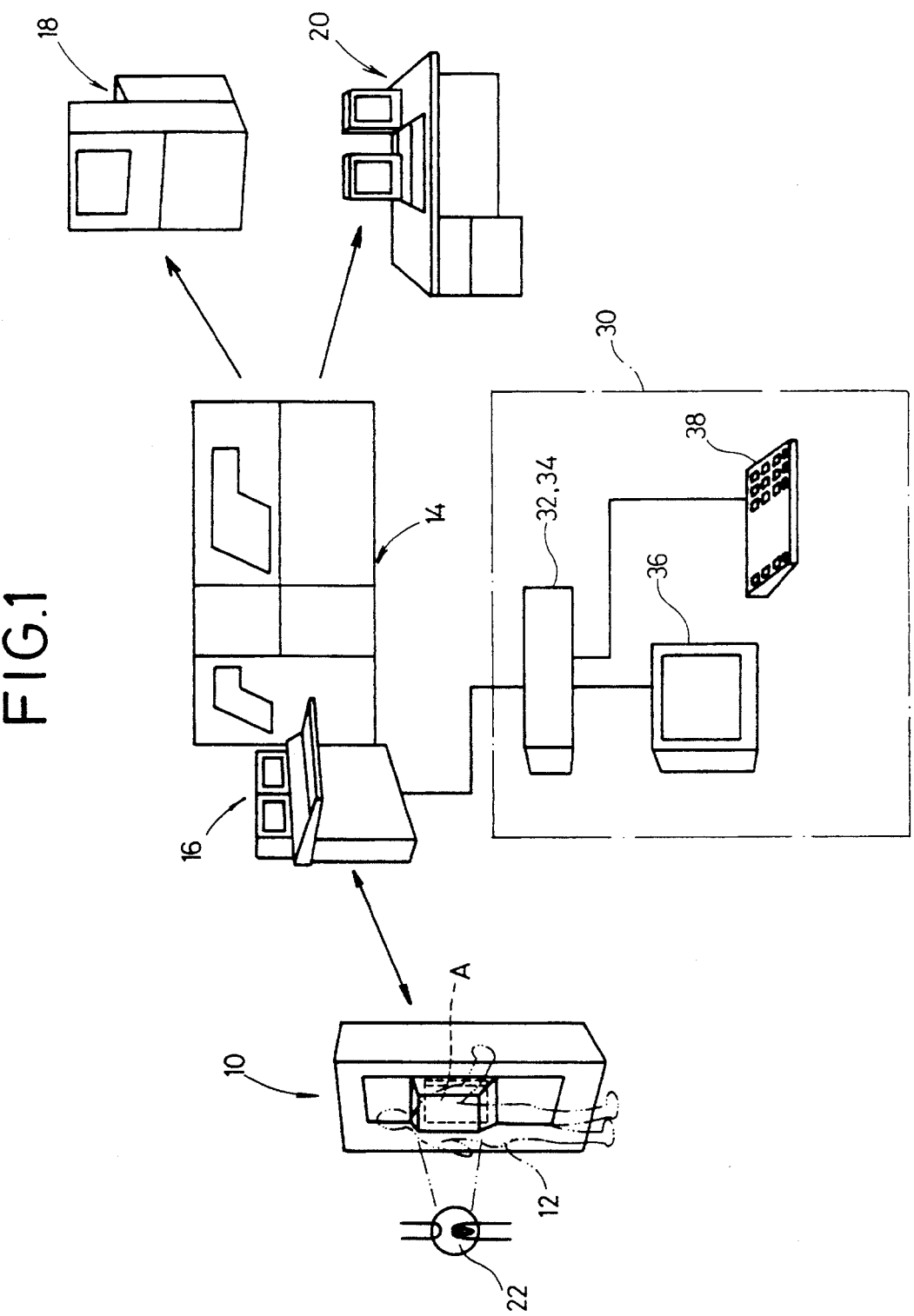
FIG. 1 is a schematic perspective view showing an overall construction of a radiation image information processing system to which a support apparatus according to one embodiment of the present invention, which is suitable for use with the radiation image information processing system, is applied.

FIG. 1 shows a radiation image information processing system and a support system therefor according to the present embodiment. The radiation image information processing system basically comprises an image reading apparatus 14 for photoelectrically reading, under predetermined conditions, a storage type phosphor sheet A on which the radioactive-ray transmitted image of an object 12 obtained by an exposure device 10 is recorded, by making use of a photoelectric transfer means, and for converting the read image into a digital signal, thereby to transmit the same, a control apparatus 16 for controlling the operation of the image reading apparatus 14 and for subjecting an image signal as a digital signal to image processing such as gradation and frequency processing, to thereby transmit the resultant signal, an image output apparatus 18 for recording the image signal as a visible image on a photographic film or the like as a photographic photosensitive material, to thereby output the recorded image signal therefrom, and another image output apparatus 20 for displaying the image signal as a visible image on a CRT or the like. Incidentally, the exposure device 10 also includes an X-ray source 22 and is adapted to store and record the radioactiveray transmitted image of the object 12 on the storage type phosphor sheet A.

The image reading apparatus 14 comprises a mechanism for applying stimulating rays such as a laser beam to the storage type phosphor sheet A and converting accelerated light emitted from a storage type phosphor of the sheet A into an image signal with an unillustrated photomultiplier, and also a mechanism for applying erasing light to the storage type phosphor sheet A from which the image signal has been read, thereby to erase any remaining image information from the sheet A so that the sheet A can be used again. The image output apparatus 18 irradiates an unillustrated photographic film such as a photographic photosensitive material with a laser beam based on the image signal obtained from the image reading apparatus 14, and develops the image on the film into a visible image.

Figure 2:
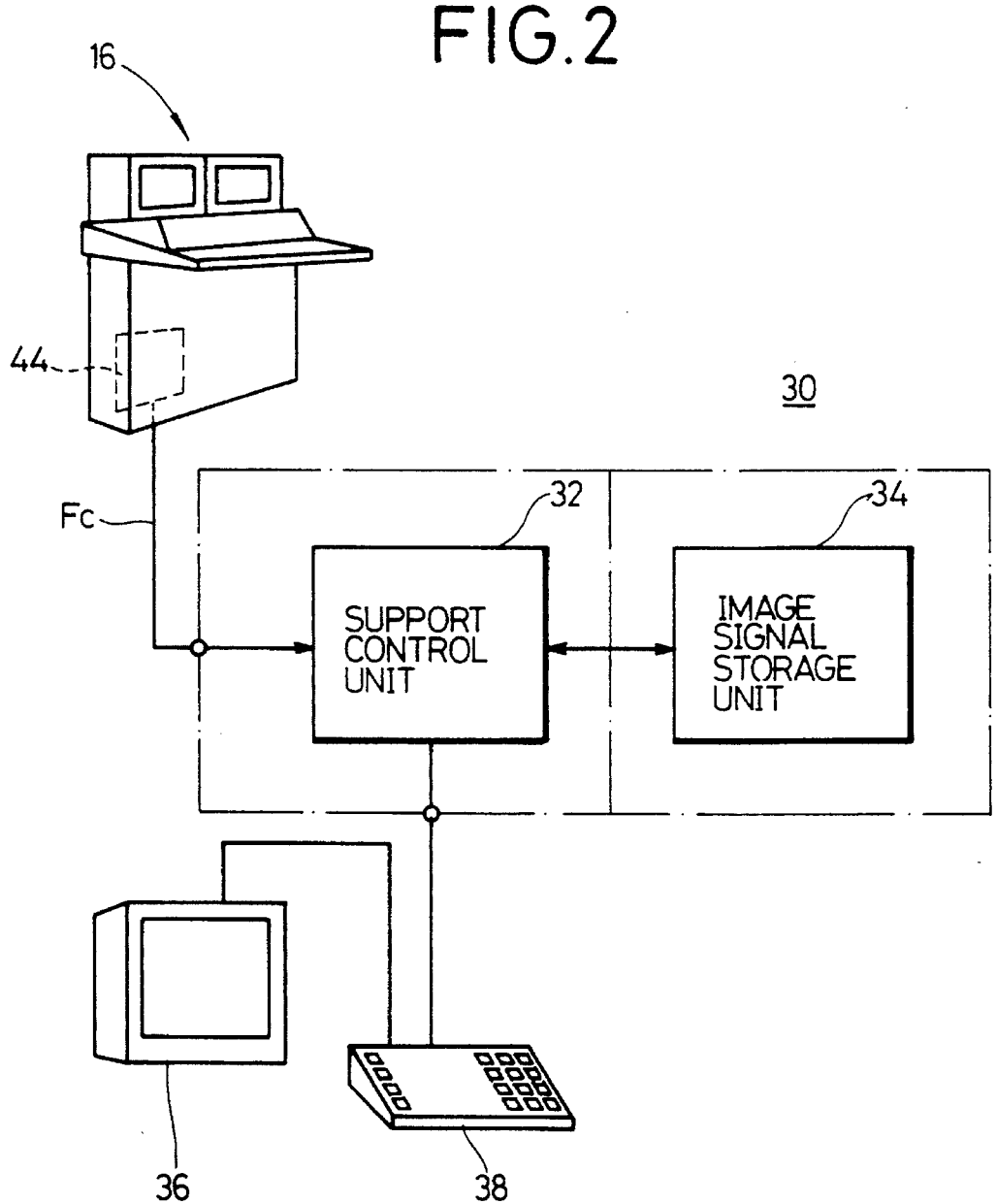
FIG. 2 is a simplified illustration of the support apparatus shown in FIG. 1.
Figure 3:
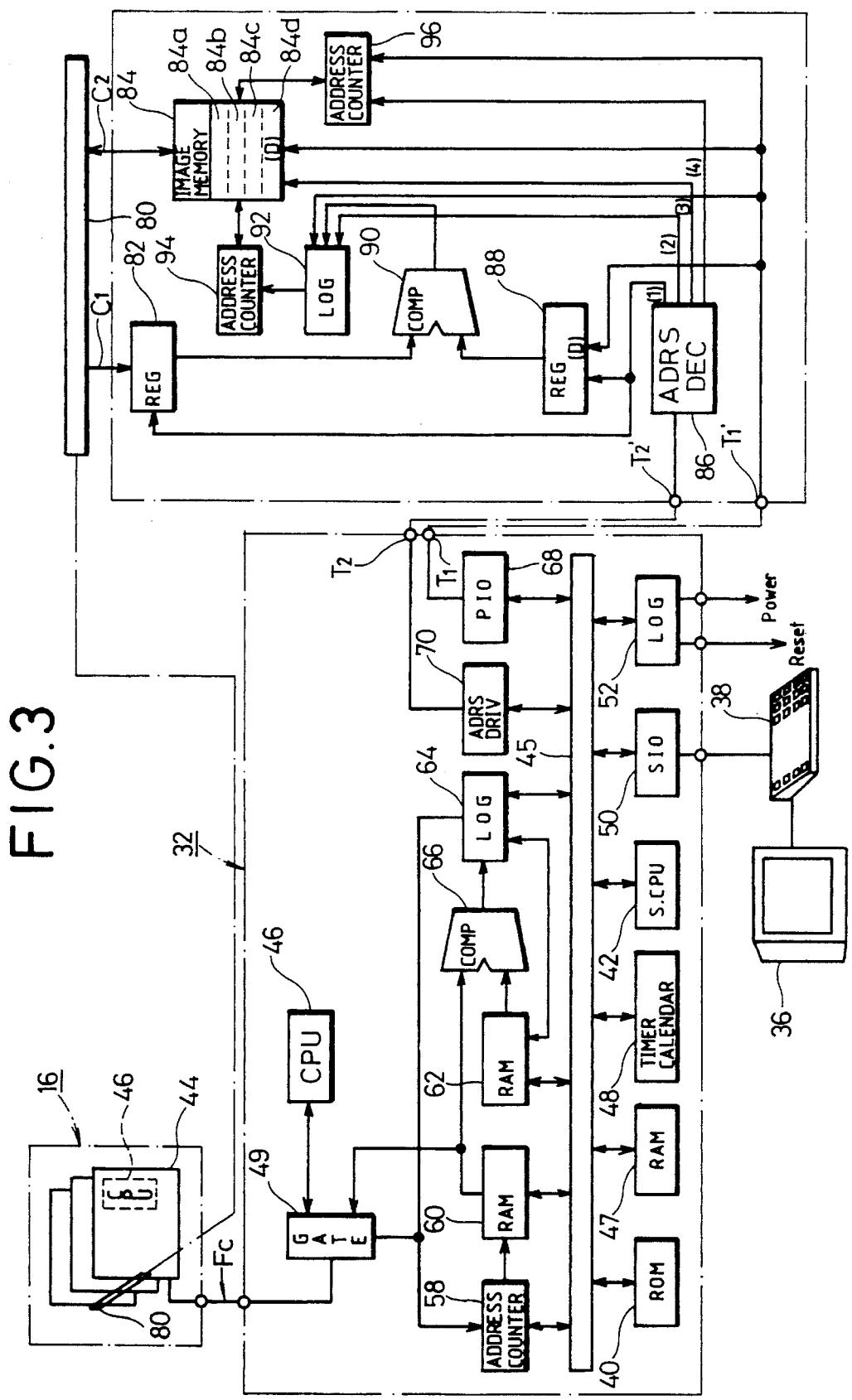
FIG. 3 is a circuit block diagram depicting one embodiment of the support apparatus shown in FIG. 2.

As shown in FIG. 2, the support apparatus 30 according to the present embodiment roughly comprises a support control unit 32, an image signal storage unit 34 for recording and holding image signals corresponding to, for example, four sheets, a display 36 equipped with a CRT or the like for displaying various types of image information thereon and a keyboard 38 for establishing functions of various kinds and for performing signal processing in the display 36. FIG. 3 is a block diagram showing the construction of the support apparatus in detail.

The support control unit 32 is connected to a control board 44 which constitutes the control apparatus 16 shown in FIG. 1. At this time, a CPU 46 for controlling the operation of the control apparatus 16 is removed from the control board 44 and mounted onto the support control unit 32. The support control unit 32 and the control board 44 are connected to each other by a flexible cable Fc through a gate 49. Supporting operation of the control unit 32 for supporting the control apparatus 16 is controlled by a support CPU (hereinafter called "SCPU") 42 based on a support program stored in a ROM 40.

The support control unit 32 has a bus line 45 to which the ROM 40 and the SCPU 42 are connected. The bus line 45 is also connected to a RAM 47 for storing a support data, a timer calendar 48 for counting a date, time or the like to thereby apply the result to data, a serial input/output controller (SIO) 50 having a function for discriminating input/output signals and a logic circuit 52. At this time, the display 36 provided with the CRT, for displaying faults or establishing data by way of example is connected to the SIO 50, together with the keyboard 38 having processing functions. Also supplied to the logic circuit 52 is signals from a reset terminal and a power supply switch. Further, the bus line 45 is also connected to an address counter 58, a RAM 60, a RAM 62 and a logic circuit 64. The address counter 58 serves to address the RAM 60 based on commands from the SCPU 42 and the logic circuit 64. The RAM 60 serves to store status data such as processing addresses and their instructions, which are to be executed by the control apparatus 16 and the CPU 46, and then output the processing addresses to a comparator 66. The RAM 62 serves to store, for example, a particular address which is indicative of a fault caused in the control apparatus 16 and its instruction or the like, and also to send the particular address out of these data to a comparator 66. The comparator 66 compares the processing addresses and the particular address, and delivers a signal representing the result of comparison to the logic circuit 64. The logic circuit 64 serves to output a shutdown command (WAIT signal) via the gate 49 to the CPU 46 based on the signal representing the result of comparison and also to send an interrupt command and a support data from the SCPU 42 to the CPU 46.

Further, the bus line 45 is connected to a PIO 68 for performing buffer operation and an address drive 70, both of which are in turn connected to their corresponding terminals $T_1$ and $T_2$ so as to send output signals thereto.

The image signal storage unit 34 includes a REG (register) 82 and an image memory 84 having a relatively mass storage capacity, both of which are connected via cables $C_1$ and $C_2$ to a bus line 80 connecting between each control board within the control apparatus 16. The image memory 84 comprises memory areas of 84a through 84d, all of which are partitioned into given address regions. An output signal from the output terminal $T_2$ of the support control unit 32 is applied through an input terminal $T_2'$ to an address decoder 86, whose first output signal is inputted to a REG 88. In addition, the first output signal and an output signal from the REG 82 are supplied to a comparator 90. An output signal from the comparator 90 and a second output signal from the address decoder 86 are respectively delivered to a logic circuit 92 and an output signal from the output terminal $T_1$ of the support control unit 32 is also supplied to the logic circuit 92 through an input terminal $T_1'$. The logic circuit 92 is connected to an address counter 94 for designating addresses for image signals, i.e., one of the four memory areas of 84a through 84d to store data in the image memory 84. A fourth output signal from the address decoder 86 and the output signal from the input terminal $T_1'$ are supplied to a read address counter 96 for reading image signals which have been stored in the image memory 84.

The support apparatus for the radiation image information processing system according to the present embodiment is basically constructed as described above. A description will next be made on operation and advantageous effects of the support apparatus.

A description will first be made on operation of the radiation image information processing system. In this case, when an X-ray is applied to the object 12 by the X-ray source 22 in the exposure device 10, the X-ray passes through the object 12 and produces a transmitted-radiation image of the object 12 on the surface of the storage type phosphor sheet A loaded in the exposure device 10. Then, the sheet A on which the image of the object is recorded is loaded into the image reading apparatus 14, where the object image is converted into image information in the form of an electric signal under the control of the control apparatus 16.

In other words, in the image reading apparatus 14, a stimulating ray such as a laser beam is applied in a main scanning direction to the storage type phosphor sheet A which is fed in an auxiliary scanning direction, accelerated light emitted from the storage type phosphor sheet A is photoelectrically read by an unillustrated photoelectric transfer means such as a photomultiplier, and the read signal is converted into image information in the form of a digital signal. When the storage type phosphor sheet A is irradiated over its entire surface with erasing light, any remaining radiation image information is erased from the sheet A from which the image information has been read, so that the storage type phosphor sheet A can be used for exposure in the exposure device 10 again.

The image information converted in the form of an electric signal by the image reading apparatus 14 is subjected, as needed, to processing such as gradation processing, frequency processing, etc., by the control apparatus 16. Thereafter, the image information is rendered visible by the image output apparatus 18 or 20 to thereby display the resultant visible image on a screen. At this time, in the image output apparatus 18, a laser beam, which is modulated by the image information, is applied in the main scanning direction to a photographic film as a photographic photosensitive material, which is fed in an auxiliary scanning direction, thereby producing the image on the photographic film. Then, the image on the photographic film is developed into a visible image. In the image output apparatus 20, an object image based on the image information is displayed on a screen such as a CRT screen.

A description will next be made on operation of the support apparatus for the radiation image information processing system, which is connected to the radiation image information processing system which operates as described above.

If a fault occurs in the radiation image information processing system while it is in operation, the system performs a certain error processing procedure, and is then brought into a HALT condition. A description will here be made on one example in which such a fault occurs. The image information has been subjected to frequency processing in the radiation image information processing system, and the image information is divided by a given coefficient upon its processing. Therefore, if no coefficient is established or the coefficient is zero, the quotient becomes infinite. If such an error occurs, the system makes a jump from the processing program to a particular address, saves the contents of a status register and a control register at the time of occurrence of the error, and is thereafter brought into the HALT condition. Then, the user of the system attempts to turn on the system again for its recovery under such a state. If the system does not recover, then the user calls a serviceman.

The serviceman then connects each control circuit board in the support control unit 32 of the support apparatus 30 shown in FIG. 3 to the control apparatus 16 and also connects the image signal storage unit 34 to the bus line 80 of the control apparatus 16. Namely, the serviceman removes the CPU 46 from the control board 44 which constitutes the control apparatus 16 and mounts the CPU 46 on the support control unit 32. Then, the serviceman connects the support control unit 32 to the control board 44 with a flexible cable Fc through the gate 49, and also connects the REG 82 of the image signal storage unit 34 and the image memory 84 to the bus line 80 of the control board 44 with the cables $C_1$ and $C_2$. Then, the serviceman establishes, with respect to the support control unit 32, a fault address at the time of occurrence of the error and an image transfer address corresponding to a start command address for executing the image transfer, based on the data of the status register and the control register, which have been saved on the side of the system upon occurrence of the error. The fault address and the image transfer address are inputted using the keyboard 38 with the display 36 such as a CRT, which is connected to the control unit 32, and is then loaded into the RAM 62 through the SIO 50.

After the fault address and the image transfer address have been established by the serviceman, the user restarts the system for the processing operation based on the system. At this time, the CPU 46 of the control apparatus 16 interconnects the image reading apparatus 14 and the CPU 46 in response to a select signal which is transferred through the gate 49. In addition, the control apparatus 16 and the CPU 46 are connected to the RAM 60 and the comparator 66 by the select signal.

A description will first be made on operation for storing information processed upon occurrence of a fault based on the fault address which has been established.

The processing information from the CPU 46 is transferred through the gate 49 to the control apparatus 16, which then controls the predetermined operation of the image reading apparatus 14 or the like. On the other hand, the processing information is transferred through the gate 49 to the RAM 60 and the comparator 66. At this time, the RAM 60 stores the processing information. The comparator 66 then compares an address of the processing information with the fault address stored in the RAM 62. On the other hand, the control apparatus 16 transfers control signals and address data signals through the gate 49 to the CPU 46. Similarly, these signals are also transferred through the gate 49 to the RAM 60 and the comparator 66. Then, the comparator 66 also compares the address of the processing information from the control apparatus 16 with the fault address stored in the RAM 62 in the same manner as described above.

Then, the comparator 66 successively compares the processing address from the CPU 46, the address data signal from the control apparatus 16 and the like. If it is ascertained that they coincide with the fault address which has been stored in advance in the RAM 62, or falls within a certain range of the fault address, the comparator 66 sends a fault detection signal to the logic circuit 64. At this time, the logic circuit 64 supplies a waiting signal WAIT to the CPU 46 through the gate 49, and starts to interrupt the SCPU 42 through the bus line 45, so that the CPU 46 is brought into a waiting condition. On the other hand, the SCPU 42 checks the processing information from the CPU 46, which has been stored in the RAM 60, based on an interrupt signal from the logic circuit 64, and then holds the result therein. Then, the SCPU 42 writes a jump command for jumping to the particular address, i.e., an error processing command in the RAM 60, and also writes a recovery program to avoid providing the error processing to an address of the RAM 60, which is designated by the jump command. Then, the CPU 46 is released from the waiting condition through the logic circuit 64.

Then, the CPU 46 continues the processing operation executed by the control apparatus 16 based on the recovery program stored in the RAM 60. Namely, the CPU 46 executes the recovery program in the RAM 60 through the gate 49, and applies a predetermined operation command to the control apparatus 16 through the gate 49. At this time, the control apparatus 16 continues the image processing operation or the like based on the recovery program stored in the RAM 60. According to the recovery program stored in the RAM 60, the CPU 46 also displays an error message or the like on the console of the control apparatus 16, thereby making it possible to indicate to the user that the error on the image at the time the error occurs is successfully processed.

A description will next be made on operation for storing image information to be transferred and for recording an improper image when it is found to be improper.

The comparator 66 compares the address of the processing information executed by the CPU 46, which has been transferred through the gate 49 described above, the address of the processing information from the control apparatus 16, and the image transfer address stored in the RAM 62.

Where the CPU 46 commands the control apparatus 16 to take in the processing address at the time of the image transfer, the processing address is compared with the particular address in the RAM 62. At this time, the particular address coincides with the processing address or falls within a certain range of the processing address. Therefore, the comparator 66 supplies a detection signal representing the image transfer to the logic circuit 64. The logic circuit 64 then supplies a waiting signal WAIT to the CPU 46 through the gate 49 so as to deactivate the CPU 46, and then interrupts the SCPU 42. Then, the SCPU 42 checks the contents in the RAM 60 and identifies the size and address of a transfer image. The SCPU 42 also establishes a transfer address representing the size of lines and the number of lines with respect to a DMA in the CPU 46. Further, the SCPU 42 clears the REG 82 through the PIO 68, and thereafter enables it and also sets an end address to the REG 88. Then, the SCPU 42 also enables the logic circuit 64. Furthermore, the SCPU 42 causes the CPU 46 to continue processing operation. As a consequence, the DMA is caused to start and a start in the transfer of image signals is made.

Here, the REG 82 latches each address on the bus line 80, which is in turn compared with the end address in the REG 88 by the comparator 90. The REG 82 then takes in an image signal on the bus line 80 with respect to the memory areas of 84a through 84d in the image memory 84 until both addresses coincide with each other. The comparator 90 now applies a coincidence signal to the logic circuit 92 when both addresses coincide with each other, and hence the address counter 94 is disabled to stop writing. Each image is successively written into the image memory 84 in the above-described manner. When an improper image is detected by the user, the user gives instructions through the keyboard 38 to hold the image, and the SCPU 42 receives the holding command from the user. Then, the SCPU 42 commands the logic circuit 92 to avoid the addresses located in the memory areas of 84a through 84d in the image memory 84, in which values counted by the address counter have been written therein based on the manner referred to above. When the images corresponding to four sheets at the maximum are held in the above-described manner, the subsequent storage of the image data is stopped.

The serviceman now gives instructions from the keyboard 38 through the SIO 50 to read out the processing information, which has been stored in the RAM 60 and leads to occurrence of the fault, and then saves the information thus read in a floppy disk or the like. The serviceman also commands from the keyboard 38 through the SIO 50 so as to read the improper image which has been stored and held in each of the memory areas of 84a through 84d within the image memory 84 provided in the image signal storage unit 34. As a consequence, the SCPU 42 then sets the read address counter 96 through the PIO 68 and at the same time, reads data during a cycle executed through the PIO 68, thereby to reproduce the improper image with the image output apparatus 18. Thereafter, the serviceman will find out the cause of the fault and perform a recovery processing or the like, base on the floppy disk and the reproduced image.

A description will here be made on adjustment of the system by the user, i.e., initial adjustment of the system at the time of its installation or readjustment of the system in use, with a view toward maintaining desired functions of the system using the above-described radiation image information processing system.

It is first performed by the serviceman in a service station or the like to store, in advance, the reference image information about parts to be frequently photographically recorded, such as a chest, a stomach (magen), a bone, etc., in the image memory 84, said information being recorded in an optical disk device or the like. In this case, the reference image information for desired purposes in the memory areas of 84a through 84d of the image memory 84 is stored by using the optical disk device, romwriter, etc. The provision of a plurality of image memories 84 for such reference image information permits the use of multi-purpose reference image information. Incidentally, a method of storing information, which is employed in the romwriter or the like, has already been known and its detailed description will therefore be omitted.

Then, the serviceman electrically connects each control circuit board in the support control unit 32 of the support apparatus 30 to the control apparatus 16 in a manner similar to the above-described processing at the time the error occurs, and also connects the image signal storage unit 34 to the bus line 80 in the control apparatus 16. Then, a reference image representative of the state of the installed system, the place where it is installed, or the like, is formed based on the above reference image information. Here, a signal for reading the reference image information from the memory areas of 84a through 84d in the image memory 84 in which information about the certain parts has been stored in advance is first supplied to the address decoder 86 and the address counter 96 through the bus line 45 and the PIO 68 based on commands from the keyboard 38. The image memory 84 then supplies the reference image information about the chest, which has been stored in, for example, the memory area 84a, out of the designated memory areas of 84a through 84d, to the control apparatus 16 through the gate 49.

The serviceman then represents image information on the image output apparatus 18 and 20 with the display 36 and the keyboard 38, and the comparison and investigation of the image information is here made, whereby image processing parameters such as parameters regarding gradation processing, frequency processing, etc., are established.

At this time, the serviceman establishes a reference value where no parameters are established in advance upon installation of the system, and establishes this value as it is where the parameters have already been established upon readjustment of the system.

Based on the parameters established by the serviceman, the CPU 46 then executes the image processing with respect to the reference image signal, and outputs a visible image through the image output apparatus 18 and 20. At this time, the serviceman investigates together with doctors or the like whether or not the visible image is in a good or bad condition. According to the result of its investigation, the serviceman establishes again other image processing parameters with the keyboard 38 so as to output an image subjected to the image processing using the parameters referred to above. It is therefore possible to establish most suitable image processing parameters by repeatedly performing the operation for the above-described investigation.

Desired parameters can be recognized for each part in the form of a uniform image as a whole by establishing parameters with such a reference image, thereby to enable the serviceman to easily and promptly effect the operations of establishment for parameters.

Further, in the system according to another embodiment, the user can establish image processing parameters for producing optimal images by using the display 36 and the keyboard 38 which constitute the support apparatus 30.

In other words, the user establishes a parameter setting mode with respect to the support apparatus 30 by using the keyboard 38, and thereafter loads the image reading apparatus 14 with the sheet A on which a certain image is recorded and then starts the image reading operation. At this time, the gate 49 serves to monitor information about instructions or the like which are read out of the memory in the control apparatus 16 based on processing addresses and the above-described processing address which are outputted from the CPU 46 to the control apparatus 16, and to store the same in the RAM 60. Then, the comparator 66 compares the processing address which has been stored in the RAM 60 with a particular address for taking in the image information which has been stored in the RAM 62 by the serviceman, and the result of comparison is supplied to the logic circuit 64.

Where the CPU 46 commands the control apparatus 16 to take in a processing address at the time instructions for taking in the image information have been made, the processing address is stored in the RAM 60 and supplied to the comparator 66, where this processing address is compared with the particular address in the RAM 62. At this time, the particular address coincides with the processing address. Therefore, the comparator 66 supplies a coincidence signal to the logic circuit 64. The logic circuit 64 then supplies a waiting signal WAIT to the CPU 46 through the gate 49 to deactivate the CPU 46, and interrupts the SCPU 42. Then, the SCPU 42 checks the contents stored in the RAM 60 and identifies the size and address of a transfer image. The SCPU 42 also establishes a transfer address representing the size of lines and the number of lines with respect to a DMA in the control apparatus 16. Further, the SCPU 42 clears the REG 82, and thereafter enables it and also sets an end address to the REG 88 through the PIO 68. Then, the SCPU 42 causes the CPU 46 to continue processing operation. As a consequence, the DMA is caused to start and a start in the transfer of image signals is made.

The REG 82 latches each address on the bus line 80, and the latched address is compared with the end address in the REG 88 by the comparator 90. The REG 82 takes in image signals on the bus line 80 with respect to the memory areas of 84a through 84d in the image memory 84 until both addresses coincide with each other. When the comparator 90 now applies a coincidence signal to the logic circuit 92, the logic circuit 92 disables the address counter 94 to thereby stop writing the image signals. After the writing of one image signal in the image memory has been completed, an interruption takes place with respect to the CPU 46, thereby leading to execution of completion processing. At this time, the comparator 90 monitors the completion processing executed by the CPU 46 and then interrupts the SCPU 42 to deactivate the CPU 46. Then, the SCPU 42 commands the logic circuit 92 so as to avoid the addresses located in the memory areas of 84a through 84d in the image memory 84 in which values counted by the address counter have been written therein based on the above-described manner. The image signals are stored in the memory areas of 84a through 84d in the image memory 84 respectively in the above-described manner.

On the other hand, upon completion of storage of the image signals in the image memory 84, the user then establishes image processing parameters relative to the image signals, for example, parameters regarding gradation processing, frequency processing, etc. by using the display 36 and the keyboard 38. At this time, a signal for reading out each of certain image signals from the memory areas of 84a through 84d in the image memory 84 is supplied to the address counter 96 through the bus line 45 and the PIO 68. The image memory 84 then supplies an image signal representing the chest, which has been stored in, for example, the memory area 84a out of the designated memory areas of 84a through 84d, to the control apparatus 16.

Based on the parameters established by the user, the CPU 46 then executes the image processing with respect to the image signal representing the chest, and also outputs a visible image through the image output apparatus 18 or 20. At this time, the user investigates together with doctors or the like whether or not the visible image is in a good or bad condition. According to the result of its investigation, the user establishes again other image processing parameters with the keyboard 38 so as to output an image subjected to the image processing using the parameters established. It is therefore possible to establish most suitable image processing parameters by repeatedly performing the operation for the above-described investigation.

As a further embodiment, the CPU 46 serves to replace, for example, data on the side of the control apparatus 16 with support data which has been set in advance in the RAM 47 based on a data alternation command which has been set to the RAM 60. At this time, the control apparatus 16 continues the image processing operation because the HALT condition caused by the occurrence of the error is released. Incidentally, the CPU 46 displays information about error messages or the like, which follow on the data alternation command from the RAM 60, on the console of the control apparatus 16, and suggests an error processing procedure of the image at the time the error occurs, or the like to the user.

Where it is desired to read such a traced image, the user gives instructions through the PIO 68 from the keyboard 38 so as to read the results of the trace, which are stored and held in the respective memory areas of 84a through 84d in the image memory 84 provided in the image signal storage unit 34. The SCPU 42 then sets the reading address counter 96 through the PIO 68 and at the same time reads data during a cycle executed through the PIO 68.

The SCPU 42 also analyzes, for example, the contents of a fault relative to an image formed on the image output apparatus 18 and 20, together with information about the instructions or the like which have been stored in the RAM 60.

The user also carries the image or the like to a fault analytic agency or the like to find out the cause of the fault or take a necessary means for recovering the system.

As a still further embodiment, the serviceman also gives instructions from the keyboard 38 through the SIO 50 so as to read out the processing information, which has been stored in the RAM 60 and leads to occurrence of the fault, and then saves the thus read information in a floppy disk or the like. The serviceman also commands from the keyboard 38 through the SIO 50 so as to read the improper image which has been stored and held in each of the memory areas of 84a through 84d within the image memory 84 provided in the image signal storage unit 34. As a consequence, the SCPU 42 then sets the read address counter 96 through the PIO 68 and at the same time, reads data during a cycle executed through the PIO 68, thereby to reproduce the improper image by the image output apparatus 18. Thereafter, the serviceman will find out the cause of the fault and takes a necessary measures for recovering the system and so on, based on the floppy disk and the reproduced image.

The support apparatus, which functions as described above, can monitor the bus line 80 and the CPU 46 in the control apparatus 16, check the fault and also carried out the operation test of a new program and so on. Therefore, a description will next be made on operation for checking the fault using the support apparatus 30.

A test program for testing the bus line 80 employed in the control apparatus 16 is loaded into the RAM 60 of the support control unit 32 by the RAM. The test program is executed through the keyboard 38 provided in the support apparatus 30. At this time, the SCPU 42 controls the gate 49 and the CPU 46 processes the test program loaded in the RAM 60, to thereby start the test operation of the program.

When data appears on the bus line 80 used for the control apparatus 16 owing to operation of the CPU 46, the SCPU 42 activates the image signal storage unit 34 to store the data on the bus line 80 in the image memory 84.

When the data is of an image data at this time, the SCPU 42 controls the image signal storage unit 34 as follows. In other words, the SCPU 42 first clears the REG 82 arranged in the image signal storage unit 34 and sets an end address to the REG 88 through the PIO 68, and also enables the logic circuit 92. Then, the REG 82 latches each address on the bus line 80 and the latched address is compared with the end address from the REG 88 by the comparator 90. The REG 82 then takes in image data on the bus line 80 with respect to the image memory 84 until both addresses coincide with each other. When the comparator 90 detects the coincidence of the address on the bus line 80 with the end address, the comparator 90 applies a coincidence signal to the logic circuit 92, and hence the address counter 94 is disabled to stop writing the data in the image memory.

On the other hand, the SCPU 42 performs the same processing as that of the test program executed by the CPU 46, and supplies the processed result to the image signal storage unit 34 through the PIO 68. Then, the SCPU 42 compares the data from the support control unit 32 with the data which has been written in the image memory 84, thereby making it possible to check whether or not the image processing operation of the radiation image information processing system is in the normal condition.

According to the present invention, as has been described above, where it is desired to perform adjustment by the serviceman, i.e., the initial adjustment at the time of installation of the system or readjustment of the system while it is in operation, with a view toward properly keeping functions of the radiation image information processing system from a time-dependent change in functions of the radiation image information processing system, the support apparatus for the radiation image processing system, in which the reference image information have been stored in advance, is connected to the radiation image information processing system. An image obtained from the apparatus is then rendered visible so as to be the reference visible image to be used. Using such a reference visible image, adjustment is made such that the quality in image becomes a desirable state, in the image visual-recognition analytical work of the conditions of environment at the position where the system is installed, or in the image visual-recognition analytical work using a recording medium used for the user of the system or a device with a CRT or the like. Thus, the invention can bring about the following advantageous effects. In other words, a fine adjustment can be practiced without the need for an artificial body or the like subjected to the above adjustment or the like in order to carry out the above-described adjustment. Further, the work for installation of the system can rapidly performed without the need for a number of servicemen. Also desired functions of the radiation image information processing system can be achieved as rapid as possible and an economically-practicable demand for the adjustment operation can be met.

Further, according to the present invention, the image signals or the like subjected to the fault during a predetermined period of time subsequent to connection of the support apparatus to the system are stored and held in a plurality of memory areas. The contents of the fault are thereafter analyzed based on the stored individual image signals or the like at the time the fault occurs so as to recognize, as rapid as possible, the state of the fault or the like which occurs in the radiation image information processing system, thereby removing the fault or the like. Thus, the invention can bring about an advantageous effect that the recovery of the fault or the like can be practiced as economically as possible.

Furthermore, according to the present invention, where it is desired to establish the image processing parameters employed in the radiation image information processing system, the support apparatus which is capable of storing the image signals is connected to the system, and image signals obtained as a result of a reading are temporarily stored. Thereafter, desired image processing parameters are established from the optimal image obtained by processing the stored image signals based on various image processing parameters. At this time, the image processing parameters capable of obtaining the optimal image can be established by the user himself. Since the image processing can repeatedly be practiced with respect to the stored image signals, no burden is imposed on the patients. This process is therefore preferred.

Besides, according to the present invention, the support control unit and the bus monitor board are connected to the radiation image information processing system so as to monitor data on the bus line, thereby making it possible to monitor the fault of the system or carry out the operation test of the new program, or the like in detail.

Having now fully described the invention, it will be apparent to those skilled in the art that many changes and modifications can be made without departing from the spirit or scope of the invention as set forth herein.

What is claimed is:

1. A correction apparatus for use with a radiation image information processing system, said correction apparatus being connected to a radiation image information processing system which subjects a radiation image to signal processing so as to obtain an image signal and generates a visible image from the image signal, said correction apparatus comprising:

a control unit for detecting a fault in operation of the radiation image information processing system in accordance with first data resulting from execution of a test program by the radiation image information processing system, wherein said test program is stored in said control unit;

said control unit further comprising a processing means for independently executing said test program producing second data which are compared to said first data to determine whether the radiation image information processing system is operating without faults; and image signal storing means, coupled to said radiation image information processinq system via a data bus and to said control unit, for storing image signals.

2. The correction apparatus according to claim 1, wherein said control unit comprises first storing means for storing a test program therein, and said image signal storing means includes second storing means for storing data produced by said radiation image information processing system by executing said test program and supplied to said second storing means on a bus line connected between the radiation image information processing system and said second storing means, and wherein detection of a fault in said radiation image information processing system is determined from said data stored in the second storing means.

3. The correction apparatus according to claim 2, wherein said second storing means includes an image memory.

4. The correction apparatus according to claim 1, wherein said image signal storing means stores said first data and said second data, said control unit further comprising:

first memory means for storing a test program which is executed by said radiation image information processing system and said processing means;

testing means for initiating supply of said test program to said radiation image information processing system and to said processing means to begin a testing operation;

comparing means for comparing said first data and said second data received from said image signal storing means; and means for judging whether said radiation image information processing system is defective based upon information from said comparing means.

5. A correction apparatus for use with a radiation image information processing system which subjects a radiation image to certain signal processing to obtain an image signal and generates a visible image from the image signal, said correction apparatus comprising:

image signal storing means for storing image signals and at least one predetermined reference image signal; and a control unit, connected to said image signal storing means, for selectively sending said at least one predetermined reference image signal to said radiation image information processing system for processing to produce said visible image to be used for detecting a fault in said radiation image information processing system and for initial adjustment and subsequent readjustment of said radiation image information processing system.

6. The correction apparatus according to claim 5, wherein said control unit comprises supplying means for initiating supply of said at least one predetermined reference image signal stored in said image signal storing means to the radiation image information processing system, and parameter establishing means for establishing each of image processing parameters relative to the image signal supplied to the radiation image information processing system.

7. The correction apparatus according to claim 6, wherein said control unit further comprises storing means including an image memory, and wherein said parameter establishing means includes a keyboard.

8. The correction apparatus according to claim 6, wherein said image signal storing means comprises an image signal selecting means, responsive to an output signal received from said supplying means in said control unit, for selectively reading out an image signal stored in said image signal storing means upon the initial adjustment and subsequent readjustment, and image signal supplying means for supplying the image signal stored in said image signal storing means to said radiation image information processing system to generate the visible image.

9. The correction apparatus according to claim 8, wherein said correction apparatus further comprises:

means for initiating selection of the image signal stored in said image signal storing means; and means for adjusting image processing parameters in accordance with an appearance of said visible image.

* * * * *